(12) United States Patent
Sickenberger et al.

(10) Patent No.: US 7,375,348 B1
(45) Date of Patent: May 20, 2008

(54) MICRO UV DETECTOR

(75) Inventors: David W. Sickenberger, Bel Air, MD (US); Jerry B. Cabalo, Towson, MD (US); Richard Sickenberger, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 216 days.

(21) Appl. No.: 11/268,758

(22) Filed: Nov. 3, 2005

Related U.S. Application Data (60) Provisional application No. 60/659,119, filed on Mar. 7, 2005.

(51) Int. Cl.
*G01N 21/64* (2006.01)
*G01N 15/10* (2006.01)
*G01N 15/14* (2006.01)

(52) U.S. Cl. .................. 250/461.2; 250/575; 250/573; 356/336; 356/338; 359/361; 324/464

(58) Field of Classification Search ...................... None
See application file for complete search history.

(56) References Cited

U.S. PATENT DOCUMENTS 5,254,861 A * 10/1993 Carpenter et al. .......... 250/573
6,140,653 A * 10/2000 Che ........................ 250/458.1
6,967,338 B1 * 11/2005 Sickenberger et al. ... 250/461.1

OTHER PUBLICATIONS

Kopp, Christophe et al. "Micro-chip laser—a comparison between gradient-index lens and ball-lens for pump-laser diode coupling", Optics Communications 235, Elsevier (Jan. 22, 2004), pp. 175-182.*

* cited by examiner

*Primary Examiner*—Constantine Hannaher
*Assistant Examiner*—Yara B Green
(74) *Attorney, Agent, or Firm*—Ulysses John Biffoni (57) ABSTRACT

A biological aerosol detector is provided. The biological aerosol detector uses a semiconductor optical source with an ultraviolet emission band to excite biological molecules in an aerosol sample. Filtering optics are configured to attenuate radiation from a secondary emission band of the optical source to prevent false signals due to scattering of secondary emission band radiation from non-biological molecules. An intake/exhaust manifold that includes an intake pipe that fits within a concentric exhaust pipe is also provided. The intake/exhaust manifold planarizes the flow of the sampled aerosol to maximize the time of irradiation. An electrostatic sampling grid is also provided to selectively draw biological molecules having a net charge into the optical chamber.

19 Claims, 5 Drawing Sheets

GRAPHITE ORIFICE

MICRO UV DETECTOR

RELATED APPLICATIONS

Applicant claims the benefit under 35 U.S.C. § 119(e) of provisional application Ser. No. 60/659,119 filed Mar. 7, 2005.

GOVERNMENTAL INTEREST

The invention described herein may be manufactured, used and licensed by or for the U.S. Government.

TECHNICAL FIELD

This document relates to detection of aerosols by illumination with ultraviolet radiation.

BACKGROUND

The detection of aerosols within fluid samples can be accomplished by optical methods. Such methods are useful in detecting potentially harmful aerosols, such as biological aerosols that may be present after a biological agent attack or industrial accident. It is well known that biological molecules fluoresce when excited by ultraviolet (UV) radiation. As a result, biological molecules in an aerosol sample can be optically detected by irradiating the sample with ultraviolet radiation, and observing the fluorescence response. Since differing excitation wavelengths may be used to detect different classes of biological molecules, the excitation wavelength can be chosen to detect specific classes of biological molecules such as proteins, flavinoids, and metabolite products.

A biological aerosol detector of the type described above is described in more detail in U.S. patent application Ser. No. 10/720,877, now allowed, which is incorporated herein by reference. The detector described in patent application Ser. No. 10/720,877, includes a light source 4, which can be a UV laser light source or an LED light source. Recently, UV light sources in the form of semiconductor ultraviolet optical sources or SUVOS have become available. These light sources typically have both a primary emission band with a center wavelength in the ultraviolet region (i.e., a primary emission band that is capable of eliciting a fluorescence response from a biological aerosol), and a secondary emission tail at longer wavelengths that overlaps and interferes with the fluorescence response. When SUVOS type light sources are used in the biological aerosol detector described in patent application Ser. No. 10/720,877, light from the source's secondary emission band can be scattered by particles in the aerosol detector's optical cavity, thereby creating a positive response signal in the aerosol detector regardless of whether the scattering particle was a biological molecule or not. To reduce the occurrence of these types of false positive signals, the radiation from the SUVOS's secondary emission band must be attenuated to prevent it from entering the aerosol detector's optical cavity.

SUMMARY

A biological aerosol detector is provided. In one aspect, the biological aerosol detector includes an optical excitation source having a primary emission band and a secondary emission band. The excitation source can be a semiconductor ultraviolet optical source with a primary emission band in the ultraviolet spectrum, and a secondary emission band at longer wavelengths. The primary emission band is configured to excite biological molecules in an aerosol sample in the detector's optical cavity. Filtering optics are included to attenuate radiation that is emitted in the secondary emission band which, when scattered, can mimic the fluorescence response of a biological molecule. The filtering optics can include a dichroic mirror configured to reflect radiation in one of the primary or secondary emission bands, and to transmit radiation in the other of the primary or secondary emission bands. A focusing optic, such as a ball lens, can be positioned in the optical path between the excitation source and the dichroic mirror. The filtering optics can include an optical filter positioned in the optical path between the dichroic mirror and the optical cavity to attenuate the intensity of radiation in the secondary emission band. The filtering optics can also include a lens positioned in the optical path between the dichroic mirror and the optical filter. An orifice, located in a housing that encloses the optical cavity, can be configured as a control aperture to limit stray radiation from entering the optical cavity. The orifice can be made of any material with a UV absorbing coating, e.g., graphite.

In another aspect, the biological aerosol detector can include an optical excitation source, an optical cavity in which a sampled aerosol is irradiated by the optical excitation source, a housing that encloses the optical cavity, and a combined intake and exhaust gas manifold that passes through the housing and into the optical cavity. The combined intake and exhaust gas manifold can collect an aerosol sample and direct it into the optical cavity, and can exhaust the aerosol sample from the optical cavity after it has been irradiated by the optical excitation source. The sampling, transport, and exhaust of the aerosol can occur in the same plane to increase the time the aerosol is irradiated by the excitation source. The combined intake and exhaust gas manifold can include an intake pipe of a first length having one end external to and one end internal to the housing forming the optical cavity, an exhaust pipe of a second length that is less than the first length, and that completely surrounds the intake pipe over at least a portion of the length of the intake pipe, and an end cap. The end cap can cover the end of the exhaust pipe that is external to the housing, and can include a face plate with a hole in it that allows passage of the intake pipe through it.

In another aspect, the biological aerosol detector includes an optical excitation source, an optical cavity in which a sampled aerosol is irradiated by the optical excitation source, a housing that encloses the optical cavity and that has two holes that define a sampling axis, a pair of electrical grids located external to the housing and on either side of the holes forming the sampling axis, and a power source attached to the electrical grids to generate an electric field between them. The electric field across the electrical grids allows the preferential sampling of aerosol molecules having a net electrical charge. The electrical grids can be plates or meshes. The biological aerosol detector can include a Faraday based ion detector to electrically detect sampled aerosol molecules. The Faraday based ion detector can include a collection grid and an ion detection circuit. The biological aerosol detector can also include an optical detection circuit to detect a fluorescence signal emitted by a sampled aerosol molecule that has been excited by the optical excitation source, and a correlation circuit to correlate signals from the optical detection circuit and the Faraday based ion detector. The correlation circuit can be a temporal coincidence circuit.

The details of one or more embodiments of the invention are set forth in the accompanying drawings and the descrip-

DETAILED DESCRIPTION

Figure 1:
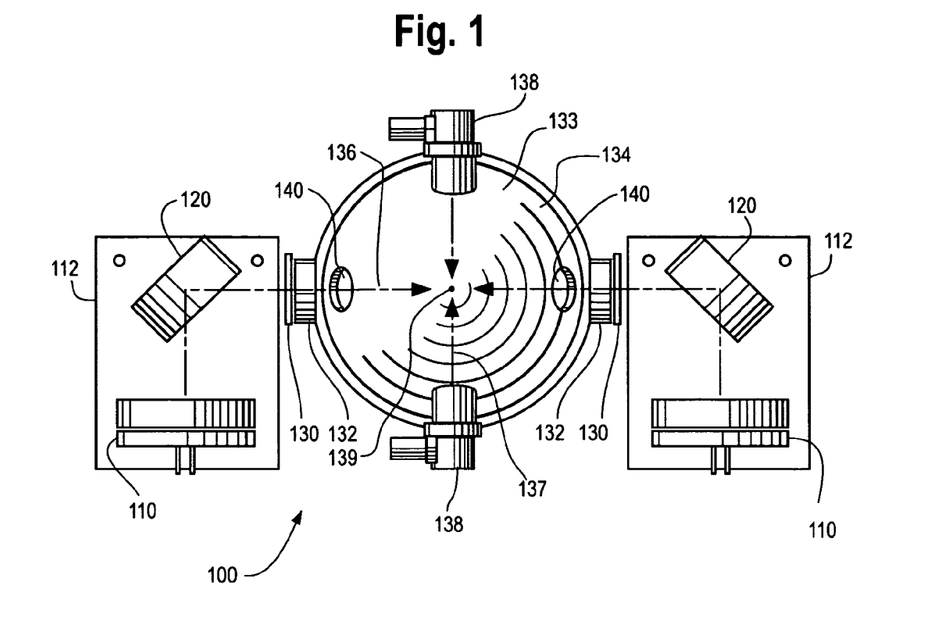
FIG. 1 is a schematic representation of a biological aerosol detector according to an embodiment of the present invention.

FIG. 1 is a schematic representation of a biological aerosol detector 100 according to one embodiment of the present invention. In one aspect, the biological aerosol detector 100 shown in FIG. 1 improves upon the biological aerosol detector described in patent application Ser. No. 10/720,877 by providing an alternative optical excitation configuration and accompanying filtering optics. The biological aerosol detector 100 has at least one excitation assembly 110 that includes an excitation source and collection/collimation optics that are discussed in more detail in connection with FIG. 2. Excitation assembly 110 emits radiation toward a dichroic mirror assembly 120 that transmits a portion of the radiation toward a beam dump 208 (FIG. 2), and reflects a portion of the radiation toward a lens 130. The excitation assembly 110 and the dichroic mirror assembly 120 are mounted on a plate 112 to allow for a fixed relative positioning of the two components. The radiation reflected from dichroic mirror assembly 120 passes through the lens 130 to a filter 132 that further reduces a portion of the radiation passing through lens 130.

The biological aerosol detector 100 also includes an optical cavity 133 formed in part by the housing for an elliptical mirror 134. An aerosol sample drawn into optical cavity 133 is excited by radiation that is emitted from excitation assembly 110 and that passes through lens 130 and filter 132. The lens 130 focuses this radiation onto the inner focal point of elliptical mirror 134, and the optical path from lens 130 to the inner focal point of elliptical mirror 134 defines a UV or excitation beam axis 136.

As shown in FIG. 1, detector 100 includes first and second excitation assemblies with corresponding filtering optics placed at opposite ends of the UV beam axis 136. This configuration allows particles to be illuminated from two optical sources, thereby providing twice the excitation power of devices that use a single excitation assembly. In addition, the wavelengths emitted by the multiple excitation assemblies 110 may be different, thereby allowing the detection of different biological aerosols or discrimination between detected aerosols.

The housing of elliptical mirror 134 includes an inlet 138 through which aerosol samples are drawn into the optical cavity formed by the housing. As described in patent application Ser. No. 10/720,877, the biological aerosol detector shown in FIG. 1 utilizes an opposing intake flow design that defines an aerosol sampling axis 137. The UV beam axis 136 is perpendicular to this aerosol sampling axis 137, and both of these axes are perpendicular to a fluorescence detection axis 139 that runs orthogonal to the top plan view of the detector that is shown in FIG. 1. A detector placed along fluorescence detection axis 139 can detect the fluorescence radiation emitted by a biological molecule in the sampled aerosol that is excited by the ultraviolet light from excitation assembly 110.

Figure 2:
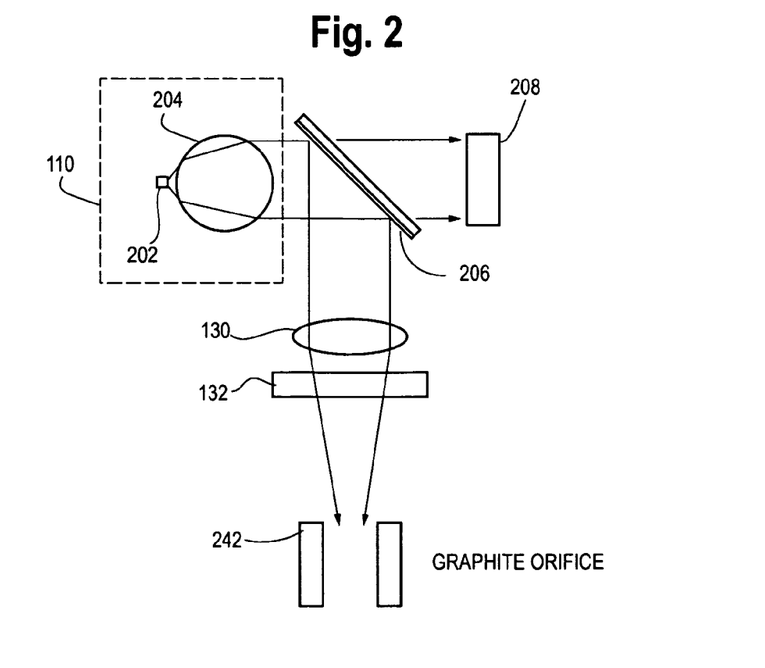
FIG. 2 is a detailed schematic representation of the filtering optics of the biological aerosol detector of FIG. 1.

FIG. 2 is a more detailed schematic representation of the excitation assembly 110 and filtering optics of biological aerosol detector 100 of FIG. 1. Excitation assembly 110 includes an excitation source 202 and a collection/collimation optic 204. The excitation source 202 is a semiconductor ultraviolet optical source or SUVOS in the form of a light emitting diode or LED. A SUVOS based LED typically emits radiation in both primary and secondary emission bands. The primary emission band, with a center wavelength in the ultraviolet region, is used to irradiate and optically excite biological molecules in an aerosol sample within the optical cavity. The secondary emission band, with a center wavelength in the visible spectrum, is generally an unintended and unwanted companion to the primary emission band since its spectrum sometimes and undesirably overlaps the expected fluorescence spectrum of biological molecules excited by radiation from the primary emission band. As a result of this overlap, radiation from the secondary emission that is scattered by non-biological molecules in the sampled aerosol can mimic or appear to be fluorescence radiation that is emitted by excited biological molecules in the aerosol.

To reduce the likelihood of such false positive signals, and to improve detector 100's ability to distinguish between biological and non-biological molecules in a sampled aerosol, detector 100 includes several features to attenuate the radiation from the SUVOS excitation source's secondary emission band. More particularly, detector 100's excitation assembly 110 includes a collection/collimation optic 204 in the form of a ball lens having a short focal length and large numerical aperture. The collection/collimation optic 204 focuses and directs radiation emitted from the SUVOS excitation source 202 onto a dichroic mirror 206. The dichroic mirror 206 reflects light within the SUVOS excitation source 202's primary emission band with high efficiency, but reflects only a small portion of light within the SUVOS source 202's secondary emission band. Instead, the majority of light in the SUVOS source 202's secondary emission band is transmitted through dichroic mirror 206 to a beam dump 208, where it is absorbed.

The radiation that is reflected from dichroic mirror 206 is reflected toward a lens 130 that focuses the radiation to the inner focal point of the elliptical mirror 134 shown in FIG. 1. Lens 130 is a 30 mm effective focal length plano-convex lens, or any other lens having a sufficiently long focal length that allows it to be positioned outside of the optical cavity 133 (FIG. 1) formed by elliptical mirror 134. An optical filter 132, positioned between lens 130 and optical cavity 133, further attenuates the radiation from the SUVOS source 202's secondary emission band while substantially transmitting the radiation from the SUVOS source 202's primary emission band. Preferably, optical filter 132 has an optical density of at least 2 with regard to the light from the secondary emission band. Optical filter 132 may be a Schott UG-11 filter, multi-layer dielectric notch filter, a colored glass filter, or any other type of filter having suitable characteristics with regard to the transmission and attenuation of the primary and secondary emission bands. The combination of dichroic mirror 206 and optical filter 132 provides a suitable compromise between maintaining high throughput of desired radiation from the SUVOS excitation source 202's primary emission band, and attenuating the unwanted radiation from the SUVOS excitation source 202's secondary emission band. The filtering optics also include a graphite orifice 242, located in the housing of the elliptical mirror 134, that serves to attenuate stray radiation that enters the opening 140 in the housing of elliptical mirror 134.

Figure 3A:
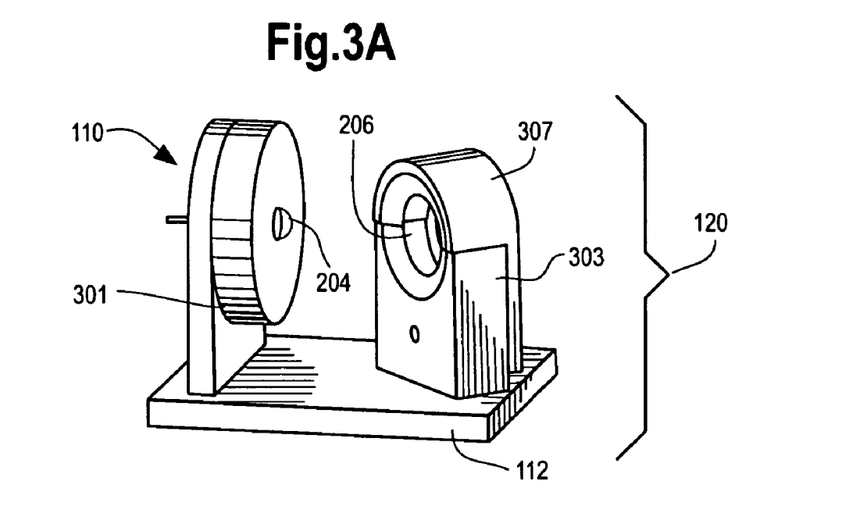
FIGS. 3A and 3B shows the excitation assembly and dichroic mirror assembly of FIG. 1.
Figure 3B:
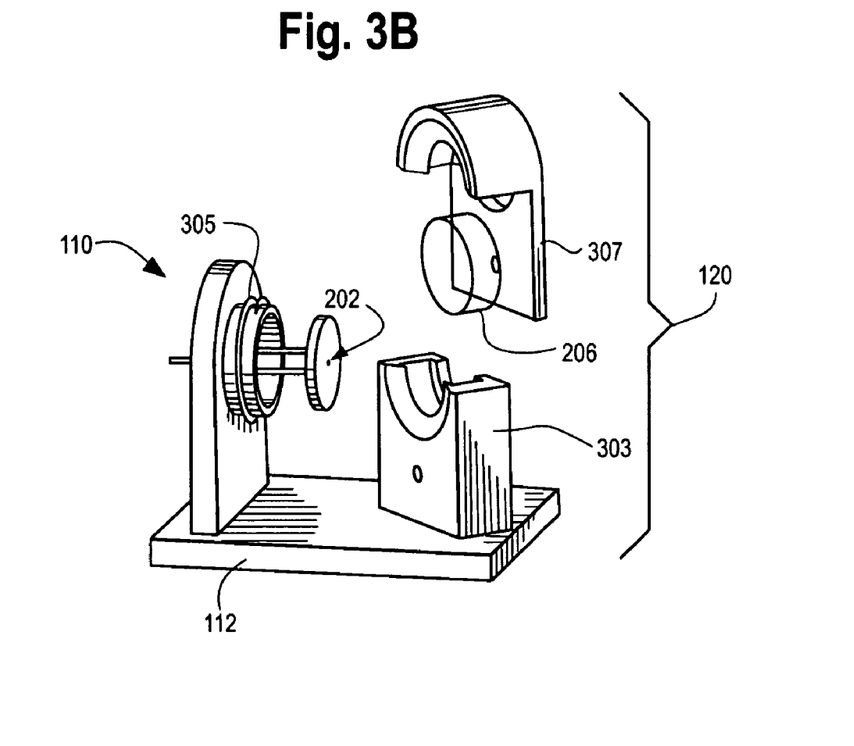

FIGS. 3A and 3B represent this embodiment of excitation assembly 110 and dichroic mirror assembly 120. Excitation assembly 110 includes a cover 301 that is mounted over a SUVOS based LED 202 (shown in FIG. 3B). Ball lens 204 is fixed to cover 301, which is mounted over SUVOS based LED 202 via threads 305 that allow radiation transmitted through ball lens 204 to be focused. Dichroic mirror assembly 120 includes a dichroic mirror 206 mounted within a lower portion 303 and upper portion 307 of a holder. Both dichroic mirror assembly 120 and excitation assembly 110 are mounted on a plate 112 to allow for a fixed relative positioning of these components.

The inlets 138 of detector 100 (FIG. 1) may be modified to serve as both the intake and exhaust ports of a sampled aerosol. Such an arrangement is shown in the combined intake/exhaust manifold 400 shown in FIGS. 4A, 4B, and 5A through 5C. Manifold 400 includes an intake pipe 401, exhaust pipe 405, and exhaust cap 403. The intake pipe 401 fits inside exhaust pipe 405, and is held in place partially by exhaust cap 403. The exhaust cap 403 includes a nozzle 409 that can be connected to a vacuum pump. The exhaust pipe 405 fits securely within an opening of the housing of elliptical mirror 134, and is made of any suitably rigid material, such as aluminum coated with an enhanced aluminum coating.

Figure 4A:
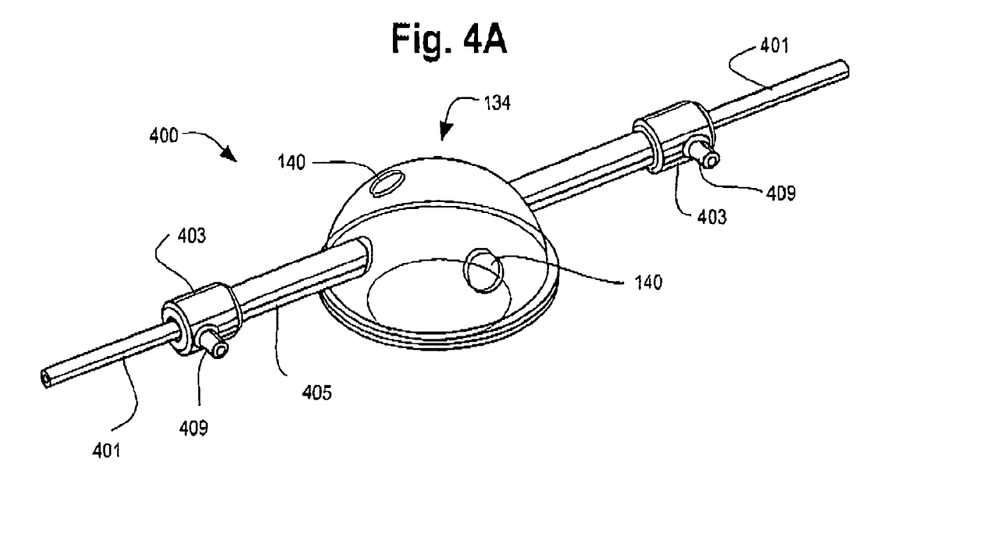
FIGS. 4A and 4B illustrate an intake/exhaust configuration of a biological aerosol detector according to an embodiment of the present invention.
Figure 4B:
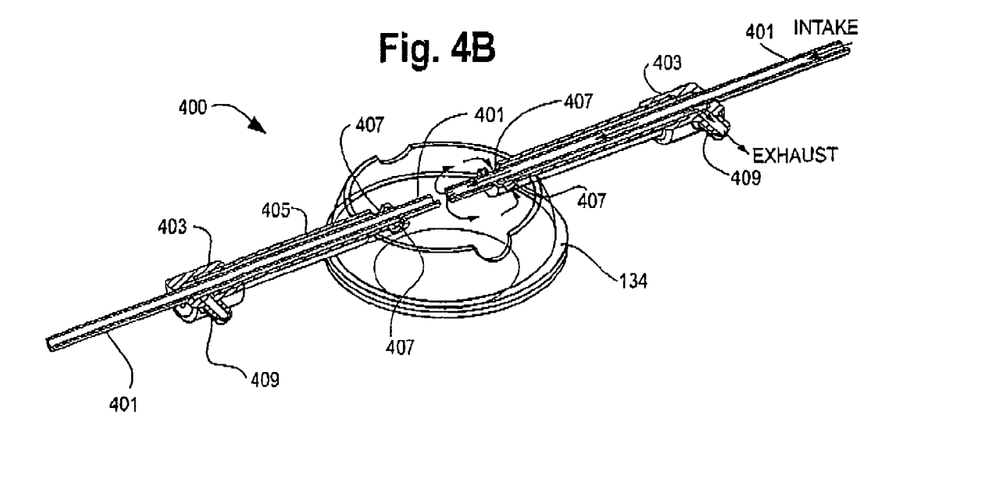

As indicated by the reference arrows shown in FIG. 4B, an aerosol sampled through intake pipe 401 flows toward the inner focal point of elliptical mirror 134. To maximize the time the sampled aerosol is exposed to radiation from the excitation assembly 110 (see FIG. 1), flows from opposing intake pipes 401 are typically collided at the focal point of elliptical mirror 134, and thereby stalled. Eventually, the sampled aerosol is evacuated from the optical cavity formed by elliptical mirror 134 through holes 407 bored through either side of exhaust pipe 405. The evacuated aerosol flows along the cylindrical gap between the outer wall of intake pipe 401 and the inner wall of exhaust pipe 405 and exits the exhaust pipe through the nozzle 409 of the exhaust cap 403. This arrangement of the inflow and exhaust trajectories of the sampled aerosol, which is largely planar in nature, reduces the vertical motion of sampled aerosol molecules. The reduced vertical motion allows the sampled aerosol molecules to remain in the optical cavity formed by elliptical mirror 134 for a longer period of time, thus increasing the likelihood of exciting and detecting any biological molecules in the sampled aerosols.

Figure 5A:
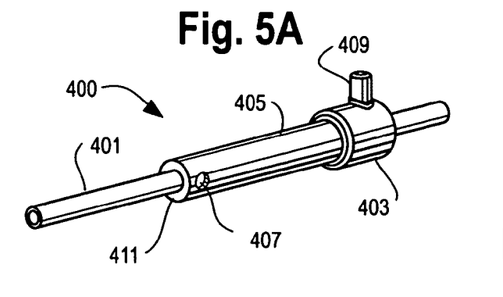
FIGS. 5A-5C illustrate component views of the intake/exhaust configuration of FIGS. 4A and 4B.
Figure 5B:
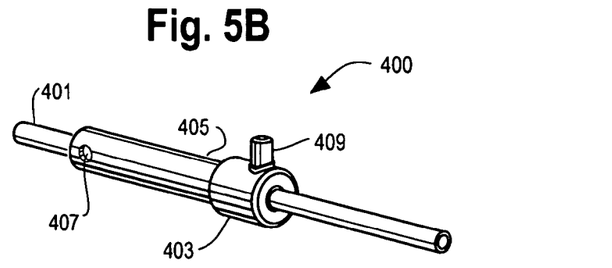
Figure 5C:
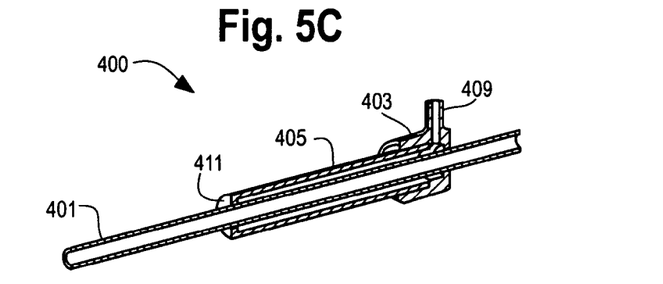

As shown in FIGS. 5A and 5B, intake pipe 401 fits within exhaust pipe 405 and exhaust cap 403. Holes 407 are bored through exhaust pipe 405. As illustrated in the cutaway view shown in FIG. 5C, intake pipe 401 is secured within exhaust pipe 405 by exhaust cap 403 on one end, and by a plate 411 that is fastened to the end of exhaust pipe 405 on the other end. Plate 411 has a hole bored through it with a diameter that is approximately equivalent to the outer diameter of intake pipe 401, so that intake pipe 401 fits securely within exhaust pipe 405.

Figure 6:
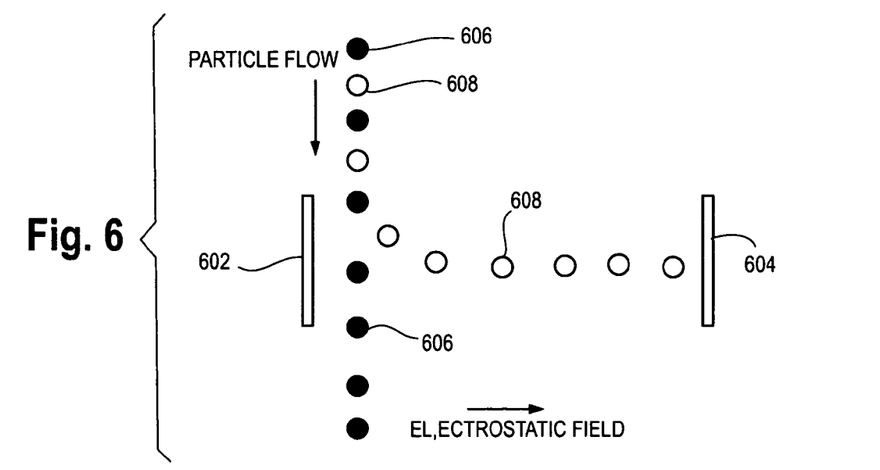
FIG. 6 illustrates the principle of electrostatic sampling of manmade biological aerosols.
Figure 7:
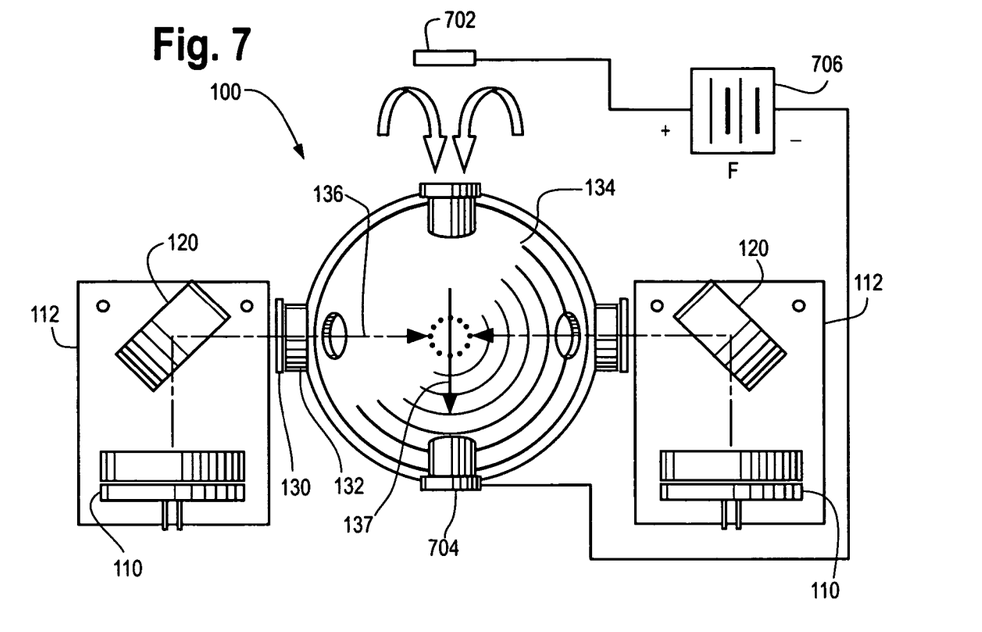
FIG. 7 illustrates the biological aerosol detector of FIG. 1 utilizing the electrostatic sampling principle of FIG. 6.

Detector 100 (FIG. 1) can also be modified to sample aerosols using an electrostatic sampling method as shown in FIGS. 6 and 7. This sampling method tends to preferentially sample biological aerosols since aerosolized biological materials tend to have a net electrostatic charge due to the manner in which they are released. Referring to FIG. 6, the basic principle behind the electrostatic sampling method utilizes an electrostatic field, such as that created by two grids 602 and 604 of differing electrostatic potential, to attract aerosol molecules with a net electrostatic charge. For example, grid 602 can be held at a positive electrostatic potential relative to grid 604, thereby creating an electrostatic field such that positively charged particles 608 (open circles) traveling between the grids will be attracted to grid 604, while neutrally charged particles 606 (black circles) will proceed along their original trajectory. Of course, the grid potentials can be reversed to attract and sample negatively charged particles rather than positively charged particles.

Referring now to FIG. 7, the detector 100 of FIG. 1 is shown modified to utilize the electrostatic sampling method discussed in connection with FIG. 6. Inlet 138 (FIG. 1) is replaced by plates 702 and 704. Plate 702 is held at a positive electrostatic potential relative to plate 704 by a direct current (DC) power source 706, thereby creating an electrostatic field between plates 702 and 704 that is directed along a sampling axis 137. The plates 702 and 704 may each include a hole to allow charged particles to pass through them. Alternatively, screens could be used in place of plates 702 and 704 for this purpose. The electrostatic field created by plates 702 and 704 draws positively charged particles into the optical cavity formed by elliptical mirror 134, so that the particles can be irradiated by ultraviolet radiation along the UV beam axis 136. The particles proceed along the sampling axis 137 to the plate 704, where they are neutralized and collected. The field strengths required to implement the sampling method shown in FIGS. 6 and 7 depend on the charge of the particles sought to be captured, the desired velocity of the particles along the sampling axis, and any pressure difference across the sampling orifice. Typically, field strengths on the order of 200 Volts/cm are sufficient to electrostatically sample biological aerosols.

Figure 8:
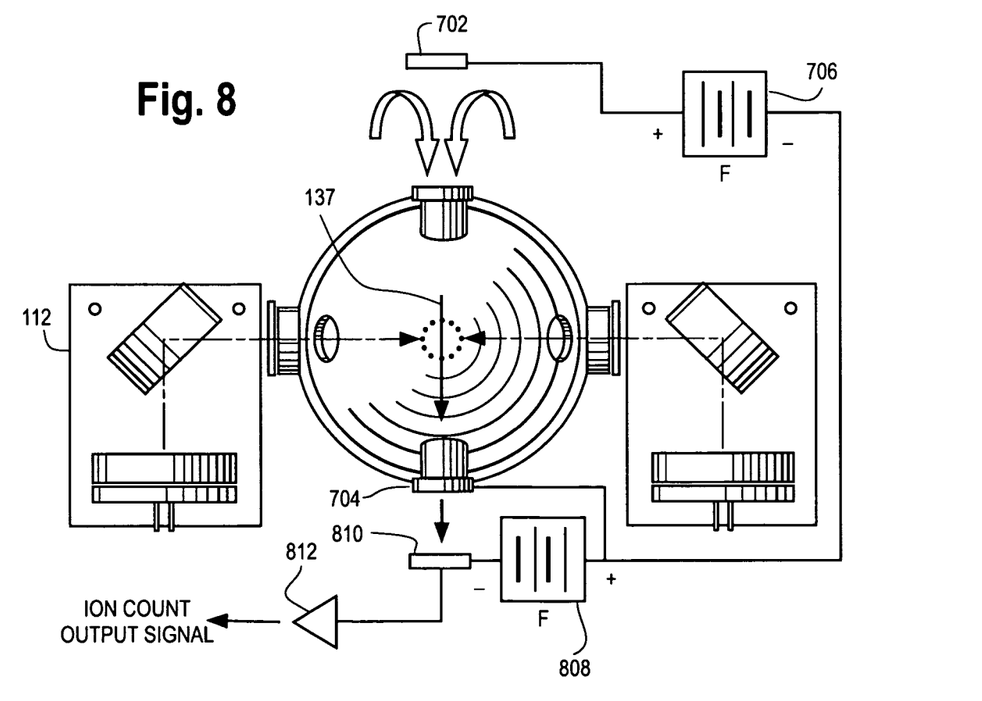
FIG. 8 illustrates the biological aerosol detector of FIG. 7 including an ion detection component.

FIG. 8 illustrates a further modification of the biological aerosol detector shown in FIG. 7. The configuration of FIG. 8 includes a collection grid 810 and a detection circuit 812 that collectively operate as a Faraday based ion detector. Plate 704 is maintained at a positive electrostatic potential relative to collection grid 810 by DC power source 808. Charged particles traveling along sampling axis 137 proceed past plate 704 to collection grid 810 where they are detected by detection circuit 812. The electrical response from detection circuit 812 can be correlated with any fluorescence signal reflected by elliptical mirror 134 onto a photodetector to further enhance the detection of biological aerosol signal events relative to background event signals. For example, the electrical response from detection circuit 812 can be put in temporal coincidence with the fluorescence signal detected by the photodetector to improve the signal to noise response of detector 100.

A number of embodiments of the invention have been described. Nevertheless, it will be understood that various modifications may be made without departing from the spirit and scope of the invention. For example, FIG. 1 illustrates one possible configuration of filtering optics for use in attenuating radiation from an optical source in an undesired secondary emission band. Other configurations, including alternative ordering of the described components, may achieve similar results and are within the spirit and scope of the present invention. For example, a dichroic mirror that largely transmits radiation from the first emission band and reflects radiation from the second emission band can be used. With this mirror the excitation source and mirror would have to be repositioned so that the reflected radiation is largely directed to a beam dump, while the transmitted radiation is largely focused to the inner focal point of the elliptical mirror 134. Also, while specific components and numbers have been given in reference to some of the filtering components, it will be understood that different components may be chosen depending on the exact wavelengths of the excitation source. Such modifications are within the spirit and scope of the present invention.

In addition, the configuration of FIGS. 6-8 has been described in connection with electrostatic fields; however, electrodynamic fields can also be used. The electrostatic sampling configuration shown in FIGS. 7 and 8 can be used in connection with the vacuum/pressure sampling flow design such as that shown in FIG. 1. In one alternate embodiment, a vacuum or pressure induced intake flow can be configured to oppose an electrostatically induced intake flow such that the two flows stall near the inner focal point of the elliptical mirror 134. Such an embodiment increases the amount of time the aerosol sample is irradiated by the excitation source, thereby increasing the likelihood that a biological molecule in the sample will be excited to a fluorescent state. Accordingly, these and other embodiments are within the scope of the following claims.

What is claimed is:

1. A biological aerosol detector comprising:
   an excitation source having a primary emission band and a secondary emission band, wherein the primary emission band is configured to excite a sample;
   an optical cavity in which the sample is excited by radiation from the excitation source;
   filtering optics configured to attenuate radiation emitted in the secondary emission band; and
   a housing for an elliptical mirror that creates the optical cavity and an orifice in the housing that acts as a control aperture to limit stray radiation from entering the optical cavity, and wherein the orifice comprises a UV absorptive material.

2. The biological aerosol detector of claim 1, wherein the excitation source is a semiconductor ultraviolet optical source and the primary emission band is within the ultraviolet spectrum.

3. The biological aerosol detector of claim 2, wherein the secondary emission band corresponds to longer wavelength emissions that overlap the emissions from a sample excited by the excitation source's primary emission band.

4. The biological aerosol detector of claim 1, wherein the filtering optics comprise a dichroic mirror configured to reflect radiation in one of the primary or secondary emission bands and to transmit radiation in the other of the primary or secondary emission bands.

5. The biological aerosol detector of claim 4, further comprising a focusing optic between the excitation source and the dichroic mirror.

6. The biological aerosol detector of claim 5, wherein the focusing optic is a ball lens.

7. The biological aerosol detector of claim 4, wherein the filtering optics further comprise an optical filter configured to attenuate the intensity of radiation in the secondary emission band.

8. The biological aerosol detector of claim 7, wherein the optical filter is positioned in the optical path between the dichroic mirror and the optical cavity.

9. The biological aerosol detector of claim 7, wherein the filtering optics further comprise a lens positioned in the optical path between the dichroic mirror and the optical filter.

10. The biological aerosol detector of claim 1, wherein the UV absorptive material is graphite.

11. The biological aerosol detector of claim 1, wherein the orifice is located at least partially within the optical cavity.

12. A biological aerosol detector comprising:
    an optical excitation source;
    an optical cavity in which a sampled aerosol is irradiated by the optical excitation source;
    a housing, enclosing the optical cavity; and
    a combined intake and exhaust gas manifold passing through the housing and into the optical cavity, wherein the combined intake and exhaust gas manifold collects the sampled aerosol and directs it into the optical cavity, and exhausts the sampled aerosol from the optical cavity, and wherein the combined intake and exhaust gas manifold samples the aerosol and directs it into the optical cavity and exhausts the sampled aerosol from the optical cavity in the same plane, and further wherein the combined intake and exhaust gas manifold further comprises:
    an intake pipe of a first length having one end external to and one end internal to the housing forming the optical cavity;
    an exhaust pipe of a second length that is less than the first length, having one end external to and one end internal to the housing forming the optical cavity the exhaust pipe completely surrounding the intake pipe over a portion of the length of the intake pipe lying between the ends of the intake pipe.

13. The biological aerosol detector of claim 12, wherein the combined intake and exhaust gas manifold further comprises an end cap having a face plate with a hole bored therethrough, wherein the end cap covers the end of the exhaust pipe that is external to the housing, and wherein the intake pipe passes through the hole bored through the end cap's face plate.

14. A biological aerosol detector comprising:
    an optical excitation source;
    an optical cavity in which a sampled aerosol is irradiated by the optical excitation source;
    a housing, enclosing the optical cavity having two holes bored therethrough along a line that forms a sampling axis;
    a pair of electrical grids located external to the housing and on either side of the holes that form the sampling axis; and
    a power source attached to the pair of electrical grids to generate an electric field between the pair of electrical grids, the electric field causing the preferential sampling of aerosol molecules having a net electrical charge.

15. The biological aerosol detector of claim 14, wherein the electrical grids are plates or meshes.

16. The biological aerosol detector of claim 14, further comprising a Faraday based ion detector to detect sampled aerosol molecules having a net electrical change.

17. The biological aerosol detector of claim 16, further comprising:

an optical detection circuit to detect a fluorescence signal emitted by a sampled aerosol molecule that has been excited by the optical excitation source; and a correlation circuit to correlate signals from the optical detection circuit and the Faraday based ion detector.

18. The biological aerosol detector of claim 17, wherein the correlation circuit is a temporal coincidence circuit.

19. The biological aerosol detector of claim 16, wherein the Faraday based ion detector comprises a collection grid and an ion detection circuit.

* * * * *